(12) United States Patent
Yu et al.

(10) Patent No.: US 11,637,527 B2
(45) Date of Patent: Apr. 25, 2023

(54) BROADBAND WIRELESS SYSTEM FOR MULTI-MODAL IMAGING

(71) Applicants: The General Hospital Corporation, Boston, MA (US); Board of Trustees Michigan State University, East Lansing, MI (US)

(72) Inventors: Xin Yu, Tübingen (DE); Chunqi Qian, Okemos, MI (US)

(73) Assignees: The General Hospital Corporation, Boston, MA (US); Board of Trustees Michigan State University, East Lansing, MI (US)

( * ) Notice: Subject to any disclaimer, the term of this patent is extended or adjusted under 35 U.S.C. 154(b) by 0 days.

(21) Appl. No.: 17/618,064

(22) PCT Filed: Jun. 12, 2019

(86) PCT No.: PCT/EP2019/065410
§ 371 (c)(1),
(2) Date: Dec. 10, 2021

(87) PCT Pub. No.: WO2020/249210
PCT Pub. Date: Dec. 17, 2020

(65) Prior Publication Data
US 2022/0311383 A1    Sep. 29, 2022

(51) Int. Cl.
*H03B 5/12* (2006.01)
*H03J 3/18* (2006.01)
(Continued)

(52) U.S. Cl.
CPC ....... *H03B 5/1243* (2013.01); *G01R 33/3692* (2013.01); *G01R 33/4806* (2013.01);
(Continued)

(58) Field of Classification Search
CPC ....... H03J 2200/10; H03J 3/185; H03L 7/099; A61B 5/055; G01R 33/3692;
(Continued)

(56) References Cited

U.S. PATENT DOCUMENTS

| 2014/0066753 A1 | 3/2014 | Qian et al. | |
| 2022/0311383 A1* | 9/2022 | Yu | A61B 5/055 |

FOREIGN PATENT DOCUMENTS

| WO | 2005116676 A1 | 12/2005 |
| WO | 2009043034 A1 | 4/2009 |

(Continued)

OTHER PUBLICATIONS

PCT/EP2019/065410—International Search Report and Written Opinion—dated Feb. 24, 2020.
(Continued)

*Primary Examiner* — Arnold M Kinkead (57) ABSTRACT

The multi-modal imaging system, in particular for brain imaging, comprising a pump signal generator which emits at least one pump signal in the radio frequency (RF)-range with a first power P1 and a second power P2, a wireless detection unit, which comprises at least one parametric resonator circuit with multiple resonance modes, wherein the at least one parametric resonator circuit comprises at least two varactors, at least one capacitor and at least one inductance, wherein, in a first detection mode, the pump signal, having a first power P1, induces a first pump current in the at least one parametric resonator circuit, wherein the at least one parametric resonator circuit is operated below its oscillation threshold and generates a first output signal by amplifying a first input signal, which is provided due to a magnetic-resonance (MR) measurement, wherein an external receiving device receives the first output signal, wherein, in a second detection mode, the pump signal, having a second power P2, induces a second pump current in the at
(Continued)

least one parametric resonator circuit, wherein the at least one parametric resonator circuit is operated above its oscillation threshold and generates a second output signal, wherein the second output signal is modulated with a second input signal, wherein the second input signal is provided by at least one neuronal probe device, connected to the at least one parametric resonator circuit, wherein the external receiving device receives the second output signal.

15 Claims, 4 Drawing Sheets

(51) Int. Cl.
     *H03L 7/099*       (2006.01)
     *G01R 33/36*       (2006.01)
     *G01R 33/48*       (2006.01)

(52) U.S. Cl.
     CPC .......... *G01R 33/4808* (2013.01); *H03J 3/185* (2013.01); *H03L 7/099* (2013.01); *H03B 2201/0208* (2013.01); *H03J 2200/10* (2013.01)

(58) Field of Classification Search
     CPC ............ G01R 33/4808; G01R 33/4806; H03B 2201/0208; H03B 5/1243
     USPC .................. 330/165; 324/322, 318, 316, 319
     See application file for complete search history.

(56) References Cited

FOREIGN PATENT DOCUMENTS

WO        2014030084 A1     2/2014
WO    WO-2014030084 A1 *  2/2014  ....... G01R 33/34092

OTHER PUBLICATIONS

Syms, et al., "Parametric Amplification of Magnetic Resonance Images," in IEEE Sensors Journal, vol. 12, No. 6, pp. 1836-1845, Jun. 2012, doi: 10.1109/JSEN.2011.2176928.

Mandal, et al., "Adaptive and Wireless Recordings of Electrophysiological Signals During Concurrent Magnetic Resonance Imaging," in IEEE Transactions on Biomedical Engineering, vol. 66, No. 6, pp. 1649-1657, Jun. 2019, doi 10.1109/TBME.2018.2877640.

* cited by examiner

BROADBAND WIRELESS SYSTEM FOR MULTI-MODAL IMAGING

STATEMENT REGARDING FEDERALLY SPONSORED RESEARCH OR DEVELOPMENT

This invention was made with government support under EB016753 awarded by the National Institutes of Health. The government has certain rights in the invention.

CROSS-REFERENCE TO RELATED APPLICATIONS

This application is a U.S. National Stage Application filed under 35 U.S.C. § 371 of International Application No. PCT/EP2019/065410, filed Jun. 12, 2019. This application is hereby incorporated by reference in its entirety.

The invention relates to a system for imaging, in particular brain imaging, and a wireless detection unit for use in a magnetic-resonance (MR) measurement.

Modern medicine and research apply a variety of imaging techniques for the animal or human body. The group of electrobiological measurements comprises magnetic resonance imaging (MRI), functional MRI (fMRI), computer tomography (CT), and electroencephalography (EEG). In particular for neurological studies of animals as well as humans, magnetic resonance imaging (MRI), functional MRI (fMRI) and electroencephalography (EEG) are well-established imaging techniques.

Magnetic resonance imaging (MRI), or Nuclear magnetic resonance imaging (NMRI), is an imaging technique to visualize the structure and function of tissue. This imaging technique provides detailed images of the tissue in any plane and a greater contrast between the different soft tissues compared to computer tomography (CT). Thus, it is especially favorable in neurological (brain), musculoskeletal, cardiovascular and oncological (cancer) imaging. MRI utilizes a powerful magnetic field B0 to align the nuclear magnetic moments or spins, in particular of hydrogen atoms in the tissue. Wherein the nuclear spins process with the so-called Larmour frequency about the magnetic field direction like gyroscopes. By applying a radio frequency (RF)-pulse, perpendicular to said magnetic field B0, the magnetic moments are tilted away from the alignment direction. After the removal of the RF-pulse, the nuclear spins relax to their equilibrium direction. Due to the relaxation, the nuclei need to lose energy in the form of emit-ting an RF-signal. This signal is detected by a receiving coil and used for the imaging. In order to encode the axial direction, a further gradient magnetic field is applied, which causes the Larmour frequency to change linearly in the axial direction.

Standard MRI imaging is often limited by its detection sensitivity which determines the achievable spatial resolution. A better local sensitivity may be achieved by placing the detection coil in close proximity to the object of interest. Such a detection coil typically sends the received signals to an evaluation device by way of an attached coaxial cable. The presence of such cables can lead to an unwanted heating of the detection coils, due to a coupling of the RF filed from the MRI system to the cable. In order to avoid the cables, there have been attempts to wirelessly transmit MRI signals received from the detection coils. In the document WO 2009/043034 A1, such a wireless device is disclosed. The disadvantage of such a device is that it requires extra components to provide DC power source for proper operation.

Electroencephalography (EEG) is a brain activity recording technique that reads scalp electrical activity generated by brain structures. The electroencephalogram (EEG) is defined as electrical activity of an alternating type, recorded from the scalp surface after being picked up by electrodes and conductive media. When brain cells (neurons) are activated, local current flows are produced. Such currents, that flow during synaptic excitations of the dendrites of many pyramidal neurons in the cerebral cortex, may be detected by an EEG measurement. The electrical current consists mostly of Na+, K+, Ca++, and Cl-ions that are pumped through channels in neuron membranes in the direction governed by membrane potential. The measured differences of electrical potentials are caused by summed postsynaptic graded potentials from pyramidal cells that create electrical dipoles between the body of the neuron and the neural branches. In most of the cases, due to the electromagnetic (EM) interference, the EEG signal detection picks up the gradient and RF pulse signals during MRI imaging. Thus an off-line post-processing method is necessary to remove the EM interference.

The object of the invention is to provide a system for imaging, in particular brain imaging, which may facilitate different imaging techniques, and which overcomes the above-mentioned disadvantages.

The problem is addressed by a system for imaging, in particular for brain imaging, comprising a pump signal generator which emits at least one pump signal in the radio frequency (RF)-range with a first power P1 and a second power P2, a wireless detection unit, which comprises at least one parametric resonator circuit with multiple resonance modes, wherein the at least one parametric resonator circuit comprises at least two varactors, at least one capacitor and at least one inductance, wherein, in a first detection mode, the pump signal, having a first power P1, induces a first pump current in the at least one parametric resonator circuit, wherein the at least one parametric resonator circuit is operated below its oscillation threshold and generates a first output signal by amplifying a first input signal, which is provided due to a magnetic resonance (MR) measurement, wherein an external receiving device receives the first output signal, wherein, in a second detection mode, the pump signal, having a second power P2, induces a second pump current in the at least one parametric resonator circuit, wherein the at least one parametric resonator circuit is operated above its oscillation threshold and generates a second output signal, wherein the second output signal is modulated with a second input signal, wherein the second input signal is provided by at least one neuronal probe device, connected to the at least one parametric resonator circuit, wherein the external receiving device receives the second output signal.

According to the invention, the first and the second output signals are transmitted wirelessly by an emission of the first and second output signals. The first and the second output signals are preferably signals in the radio frequency (RF)-range. The necessary power supply for operation of the wireless detection unit is provided by the pump signal, which is also a signal in the radio frequency (RF)-range. Thus, there is no need to provide the wireless detection unit with a cable. The unwanted heating of the detection unit, due to the use of such coaxial cables, may be avoided. Further, the wireless detection unit does not need to be equipped with a power source in the form of a battery, which allows a simpler and cost-effective design of the wireless detection unit.

Further, the detection mode of the wireless detector may be switched, simply by varying the pump power of the pump signal. When operated at pump levels below oscillation, the parametric resonator can amplify the MRI signal. Parametric oscillation occurs when the parametric amplification compensates the loss of a resonator at one of the resonance frequencies. The parametric resonator then becomes a parametric oscillator.

In the first detection mode, the power of the pump signal has a value P1, such that the at least one parametric resonator circuit is operated below its oscillation threshold. Thus, the at least one parametric resonator circuit is operated as a parametric amplifier circuit. In this detection mode, the first input signal in the form of an NMR-signal is amplified. The first input signal/NMR-signal is preferably an RF-signal and stems from coherent precession of the nuclear magnetic moments in its mixed states.

By applying a pump signal with a value P2, the one parametric resonator circuit may be operated above its oscillation threshold. Thus, it may also be called a parametric oscillator circuit. Parametric oscillation occurs when the parametric amplification compensates the loss of a resonator at the resonance frequency. Advantageously, it is driven by varying the varactors' capacitance by varying the bias voltage. Due to the oscillation, a second output signal is generated. Preferably, the oscillation frequency is half of the frequency of the externally provided pump signal. This second output signal is preferably an RF-signal and modulated by a second input signal, wherein the second input signal is provided by a neuronal probe device, connected to the at least one parametric resonator circuit. The neuronal probe device may preferably comprise at least one EEG-probe, which detects the differences of electrical potentials due to brain activity.

Preferably, such a modulation is a modulation of the amplitude of the second output signal and/or the frequency of the second output signal. Advantageously, the second input signal is encoded as sidebands of the oscillation peak of the second output signal.

Thus, the detection mode of the wireless detection unit may easily be switched and it is possible to detect and transmit an NMR signal as well as an EEG-signal with the same device.

Advantageously, the receiving device is connected with an evaluation device which evaluates the first and the second output signal and calculates the corresponding imaging data.

The term radio frequency (RF) is understood as the oscillation rate of a magnetic, electric or electromagnetic field in the frequency range from around twenty thousand times per second (20 kHz) to around three hundred billion times per second (300 GHz).

The present invention provides a broadband wireless system for multi-modal imaging, which advantageously contributes to a new application for brain imaging in a multi-modality neuroimaging environment. In particular, it may be used in the invasive brain surgical environment when the craniotomy is required for optical fiber or electrode insertion for brain functional studies. In many cases of animal brain studies, the skull will be exposed for electrode recording or two-photon imaging for craniotomy preparation. In this case, the present invention may serve as a multi-modality signal transmission platform, including MRI and electrophysiological signals concurrently based on one electronic device, implanted on or in the skull.

This has the advantage that the distance of the RF coil detector and the tissue (brain) may be reduced, which can significantly increase the SNR for a detector with a preferably small diameter (i.e. penetrating depth). Preferably, the detector can be directly used for multisite EEG signaling detection based on the wireless resonators at different frequency bandwidth, producing a highly compatible signal transmission scheme. Advantageously, such a device can be switched to either the first (NMR) or the second (EEG) detection mode, just by alternating the pump power of the pump signal.

According to a preferred embodiment, the first input signal has a first frequency $\omega_1$, wherein the parametric resonator circuit resonates at the first frequency $\omega_1$ and generates a first input current. Advantageously, the pump signal has a third frequency $\omega_3$, wherein the parametric resonator circuit resonates at the third frequency $\omega_3$ and generates the first pump current or the second pump current, depending on the first power P1 and a second power P2. Thus, when the parametric resonator circuit is operated below the oscillation threshold, the pump signal, which serves as power source, has a power P1 and preferably a third frequency $\omega_3$.

Preferably, a varactor generates a resulting current based on the first input current and the first pump current. Preferably, the resulting current is generated by mixing the first input current and the first pump current. It is further preferable that the parametric resonator circuit resonates at a second frequency $\omega_2$, in response to the resulting current to generate the first output signal. The first output signal, also called "idler signal", preferably has the frequency $\omega_2=\omega_3-\omega_1$ or $\omega_2=\omega_3+\omega_1$. It is preferred that the first output signal mixes again with the pump signal at $\omega_3$ to create a secondary first output signal with a frequency $\omega_4$, which is essentially equal to the first frequency $\omega_1$: $\omega_4=|\omega_3-\omega_2|=|\omega_3-(\omega_3\pm\omega_1)|=|\omega_1|$. Thus, an amplified signal with the frequency $\omega_1$ may be generated and emitted by the parametric resonator circuit.

According to a preferred embodiment, the second frequency $\omega_2$ is nearly equal to the first frequency $\omega_1$, wherein the second frequency $\omega_2$ differs from the first frequency $\omega_1$ by a difference frequency $\omega_d$, which is in the range between 5 kHz to 100 kHz, preferably between 20 kHz to 80 kHz, more preferably between 40 kHz to 80 kHz. Preferably, the difference frequency $\omega_d$ is larger than the receiver bandwidth of the MRI-system. The MRI-signal is typically frequency-encoded by a spatially varying gradient field. This gradient slightly alters the precession frequencies of the nuclear spins. The bandwidth of the gradient field is typically in the range between 5 kHz to 100 kHz, preferably 50 kHz. Advantageously, the difference frequency $\omega_d$ is about 5 kHz to 20 kHz larger than the bandwidth of the gradient field. Preferably, the difference frequency $\omega_d$ is about 10 kHz larger than the bandwidth of the gradient field. Thus, given a typical bandwidth of 50 kHz, the difference frequency $\omega_d$ would preferably be 60 kHz. The advantage of such a design is that the frequencies $\omega_1$ and $\omega_2$ may conveniently be differentiated.

Advantageously, the third frequency $\omega_3$ is essentially twice the first frequency $\omega_1$. By making the idler frequency $\omega_2$ close enough to the Larmour frequency $\omega_1$, and making $\omega_3$ approximately twice $\omega_1$, it is possible for $\omega_1$ and $\omega_2$ to share a single circuit mode. Preferably, the parametric resonator circuit is then a double frequency resonator.

According to a further preferred embodiment, the system comprises a device for image processing. Preferably, the external receiving device transmits the first and/or the second output signal to the device for image processing. The first and the second output signal are received by an external receiving device. Advantageously, the external receiving device is a receiving coil. Thus, it is preferred that the transmission of the first and second output signal relies on inductive coupling between the parametric resonator circuit and the receiving coil.

According to a further preferred embodiment, the at least one parametric resonator is a parallel circuit comprising two varactors and one capacitor in the center leg of the parallel circuit. Preferably, the cathode of the first varactor is connected with the first terminal of the capacitor and the cathode of the second varactor by a first connection. It is further preferred that the anode of the first varactor is connected with the second terminal of the capacitor and the anode of the second varactor by a second connection. Advantageously, the first and the second connection form a first and a second inductance. Preferably, the at least one parametric resonator circuit is a wire loop by which the two varactors are connected, and with a center leg in which the capacitor is arranged. Preferably, said wire loop is circular.

It would be conceivable that said capacitor in the center leg has an adjustable capacitance. It is conceivable that the varactors are MOS or CMOS devices and the capacitor is a chip capacitor.

According to a further preferred embodiment, the at least one neuronal probe device is connected to the first terminal of the capacitor in the center leg of the parallel circuit. Preferably, the second terminal of the capacitor in the center leg of the parallel circuit is connected to a ground electrode, wherein the neuronal probe device may preferably comprise at least one EEG-probe, which detects the differences of electrical potentials due to brain activity.

According to a further preferred embodiment, the at least one parametric resonator circuit is embedded in a planar thin film element. Preferably, the thin film element consists of a polyimide, more preferably of a copper-clad polyimide. Advantageously, the at least one parametric resonator circuit in the form of a wire loop, by which the two varactors are connected, and with a center leg in which the capacitor is arranged, is laminated by the polyimide or another suitable material. Advantageously, such a thin film element has a diameter in the range between 2 to 20 mm, preferably between 5 to 15 mm, more preferably between 8 to 12 mm. Advantageously, such a thin film element has a thickness in the range between 1 to 6 mm, preferably between 2 to 4 mm.

According to a preferred embodiment, the system comprises an MRI scanner device that enables the visualization of organs, organ function, and/or other tissue within a body, in particular a brain of a subject. The subject may be an animal, such as a rat, a monkey or a human. The MRI scanner device preferably comprises a primary magnet that generates a uniform magnetic field that is applied across the body of the subject under observation. It is preferred that the MRI scanner device further comprises at least one smaller gradient magnet that allows the magnetic field to be altered very precisely. The at least one gradient magnet allows image "slices" of the body to be created. By altering the at least one gradient magnet, the magnetic field can be specifically encoded on a selected part of the body. Advantageously, the MRI scanner device comprises an RF-signal generator which applies a radio frequency (RF)-pulse, preferably perpendicular to the magnetic field B0 of the primary magnet. This RF-pulse causes the nuclear spins to tilt away from the alignment direction.

According to a further preferred embodiment, the wireless detection unit comprises at least two parametric resonator circuits. Preferably, the at least two parametric resonator circuits overlap spatially. Advantageously, no electrical connection exists between the two parametric resonator circuits. It is further preferred that each parametric resonator circuit is tuned to resonate at a different third frequency $\omega_{3a}$, $\omega_{3b}$, such that, by applying a pump signal with the third frequency $\omega_{3a}$, $\omega_{3b}$, one parametric resonator circuit can be activated. By such an arrangement, the field of view of the wireless detection unit may be enlarged beyond an individual detector without sacrificing detection sensitivity. The mentioned overlap of the at least two parametric resonator circuits small and has the purpose of minimizing signal voids. Preferably, only one of the at least two parametric resonators is connected with at least one neuronal probe device. It is also conceivable that more of the at least two parametric resonator circuits are connected with the neuronal probe device. Finally, it is also conceivable that all of the at least two parametric resonator circuits are connected with the neuronal probe device.

According to a further preferred embodiment, the wireless detection unit comprises four parametric resonator circuits. Preferably, said wireless detection unit is arranged in a quadrilateral. Advantageously, each resonator circuit overlaps spatially with at least one adjacent resonator circuit. It is further preferred that each parametric resonator circuit is tuned to resonate at a different third frequency $\omega_{3a}$, $\omega_{3b}$, $\omega_{3c}$, $\omega_{3d}$, such that, by applying a pump signal with a third frequency $\omega_{3a}$, $\omega_{3b}$, $\omega_{3c}$, $\omega_{3d}$, one parametric resonator circuit can be activated. By such an arrangement, the field of view of the wireless detection unit may be enlarged beyond an individual detector without sacrificing detection sensitivity. The mentioned overlap of the at least two parametric resonator circuits small and has the purpose of minimizing signal voids.

According to a further preferred embodiment, the parametric resonator circuit is sequentially or simultaneously activatable Preferably, for a simultaneous activation of at least two parametric resonator circuits, at least two different pump signals with a third frequency $\omega_{3a}$, $\omega_{3b}$, $\omega_{3c}$, $\omega_{3d}$, are used at the same time.

According to a preferred embodiment, the wireless detection unit with at least two or four parametric resonator circuits is used for focal or collateral MRI measurements of the brain. For focal measurement, the excitation slice is adjusted to excite nuclei spins, only from one side of the brain. For contralateral measurement, the excitation slice is adjusted to excite nuclei spin from both sides of the brain. Preferably, said excitation slice may be adjusted by the gradient magnetic field of the MRI system. It will highlight the specific region of interest by acquiring signals from one side, however, it is faster to acquire signals from both sides at the same time.

Preferably, in a sequential acquisition mode, only a single parametric resonator circuit is responding to the pumping frequency at $\omega_{3a}$, so that only signals detectable by this resonator are amplified. In order to observe contralateral sides of the brain without increasing total acquisition time, the imaging slices, perpendicular to the individual parametric resonator circuits, are sequentially activated. At the same time, the corresponding individual parametric resonator circuits, which are in direct contact with the image slice, are selectively activated.

Advantageously, for simultaneous acquisition mode, a slice perpendicular to two parametric resonator circuits on the contralateral sides of the brain are excited. At the same time, the two parametric resonator circuits are simultaneously activated by two pump signals at $\omega_{3a}$ and $\omega_{3b}$. The output signal at the idler frequency $\omega_3-\omega_1$ of each parametric resonator circuit is individually encoded, such that it is unique to each parametric resonator circuit. By mathematically separating their signal contributions at their respective frequency bands, the single-channel receiver is multiplexed into multiple channels, but without the need for the expensive console upgrade.

Preferably, the sequential acquisition mode and the simultaneous acquisition mode may be combined by sequentially exciting image slices perpendicular to a pair of two parametric resonator circuits at the top and bottom of the quadrilateral. For each selected slice, the input signals from the left and right sides of the quadrilateral can be simultaneously amplified. These acquisition paradigms allow to run specific imaging sequences based on the acquisition modes.

The object is also addressed by a wireless detection unit for use in a magnetic-resonance (MR) measurement, comprising at least one parametric resonator circuit with multiple resonance modes, wherein the at least one parametric resonator circuit comprises at least two varactors and at least one inductance, wherein, in a first detection mode, a pump signal, having a first power P1, induces a first pump current in the at least one parametric resonator circuit, wherein the at least one parametric resonator circuit is operated below its oscillation threshold and generates a first output signal by amplifying a first input signal, which is provided due to a magnetic-resonance (MR) measurement, wherein, in a second detection mode, the pump signal, having a second power P2, induces a second pump current in the at least one parametric resonator circuit, wherein the at least one parametric resonator circuit is operated above its oscillation threshold and generates a second output signal, wherein the second output signal is modulated with a second input signal, wherein the second input signal is provided by a neuronal probe device, connected to the at least one parametric resonator circuit.

The wireless detection unit may comprise the single features or combinations of the features described above for the system for imaging. Furthermore, the system for imaging may comprise the single features or combinations of the features described for the wireless detection unit. Further, the same advantages may apply for the wireless detection unit, as described above for the system for imaging.

According to a preferred embodiment, the first input signal has a first frequency $\omega 1$, wherein the parametric resonator circuit resonates at the first frequency $\omega 1$ and generates a first input current. Advantageously, the pump signal has a third frequency $\omega 3$, wherein the parametric resonator circuit resonates at the third frequency $\omega 3$ and generates the first pump current or the second pump current, depending on the first power P1 and a second power P2. Thus, when the parametric resonator circuit is operated below the oscillation threshold, the pump signal, which serves as power source, has a power P1 and a preferably the third frequency $\omega 3$.

Advantageously, the third frequency $\omega 3$ is essentially twice the first frequency $\omega 1$. By making the idler frequency $\omega 2$ close enough to the Larmour frequency $\omega 1$, and making $\omega 3$ approximately twice $\omega 1$, it is possible for $\omega 1$ and $\omega 2$ to share a single circuit mode. Preferably, the parametric resonator circuit is then a double frequency resonator.

According to a further preferred embodiment, the at least one parametric resonator circuit is a parallel circuit comprising two varactors and a capacitor in the center leg of the parallel circuit. Preferably, the cathode of the first varactor is connected with the first terminal of the capacitor and the cathode of the second varactor by a first connection. It is further preferred that the anode of the first varactor is connected with the second terminal of the capacitor and the anode of the second varactor by a second connection. Advantageously, the first and the second connection form a first and a second inductance. Preferably, the at least one parametric resonator circuit is a wire loop by which the two varactors are connected, and with a center leg in which the capacitor is arranged. Preferably, said wire loop is circular.

It would be conceivable that said capacitor in the center leg has an adjustable capacitance. It is conceivable that the varactors are MOS or CMOS devices and the capacitor is a chip capacitor.

According to a further preferred embodiment, the at least one neuronal probe device is connected to the first terminal of the capacitor in the center leg of the parallel circuit. Preferably, the second terminal of the capacitor in the center leg of the parallel circuit is connected to a ground electrode, wherein the neuronal probe device may preferably comprise at least one EEG-probe, which detects the differences of electrical potentials due to brain activity.

According to a further preferred embodiment, the at least one parametric resonator is embedded in a planar thin film element. Preferably, the thin film element consists of a polyimide, more preferably of a copper-clad polyimide. Advantageously, the at least one parametric resonator circuit in the form of a wire loop, by which the two varactors are connected and with a center leg in which the capacitor is arranged, is laminated by the polyimide or another suitable material. Advantageously, such a thin film element has a diameter in the range between 2 to 20 mm, preferably between 5 to 15 mm, more preferably between 8 to 12 mm. Advantageously, such a thin film element has a thickness in the range between 1 to 6 mm, preferably between 2 to 4 mm.

According to a further preferred embodiment, the wireless detection unit comprises at least two parametric resonator circuits. Preferably, the at least two parametric resonator circuits overlap spatially. Advantageously, no electrical connection exists between the two parametric resonator circuits. It is further preferred that each parametric resonator circuit is tuned to resonate at a different third frequency $\omega 3a$, $\omega 3b$, such that, by applying a pump signal with the third frequency $\omega 3a$, $\omega 3b$, one parametric resonator circuit can be activated. By such an arrangement, the field of view of the wireless detection unit may be enlarged beyond an individual detector without sacrificing detection sensitivity. The mentioned overlap of the at least two parametric resonator circuits small and has the purpose of minimizing signal voids.

According to a further preferred embodiment, the wireless detection unit comprises four parametric resonator circuits. Preferably, said four parametric resonator circuits are arranged in a quadrilateral. Advantageously, each resonator circuit overlaps spatially with at least one adjacent resonator circuit. It is further preferred that each parametric resonator circuit is tuned to resonate at a different third frequency $\omega 3a$, $\omega 3b$, $\omega 3c$, $\omega 3d$, such that, by applying a pump signal with the third frequency $\omega 3a$, $\omega 3b$, $\omega 3c$, $\omega 3d$, one parametric resonator circuit can be activated. By such an arrangement, the field of view of the wireless detection unit may be enlarged beyond an individual detector without sacrificing detection sensitivity. The mentioned overlap of the at least two parametric resonator circuits small and has the purpose of minimizing signal voids.

According to a further preferred embodiment, the parametric resonator circuits are sequentially or simultaneously activatable. Preferably, for a simultaneous activation of at least two parametric resonator circuits, at least two different pump signals with a third frequency $\omega 3a$, $\omega 3b$, $\omega 3c$, $\omega 3d$, are used at the same time.

Further advantages, aims and properties of the present invention will be described by way of the appended drawings and the following description.

Figure 1:
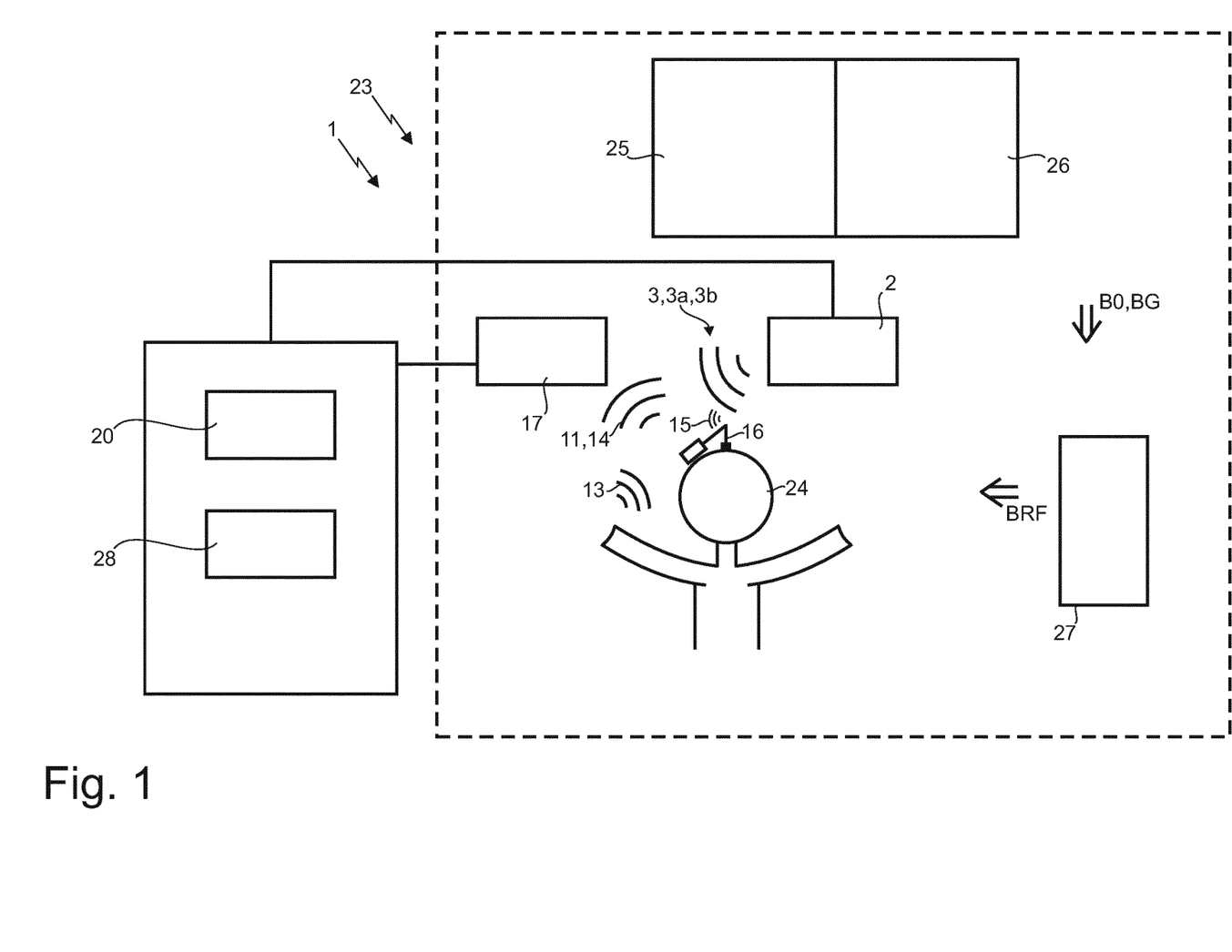
FIG. 1 shows a system for imaging, in particular for brain imaging.

FIG. 1 shows a system 1 for imaging, in particular for brain imaging, comprising a pump signal generator 2 which emits a pump signal 3, 3a, 3b in the radio frequency (RF)-range with a first power P1 and a second power P2, a wireless detection unit 4, which comprises at least one parametric resonator circuit 5 with multiple resonance modes, wherein the at least one parametric resonator circuit 5 comprises at least two varactors 6, 7, at least one capacitor 8 and at least one inductance 9, wherein, in a first detection mode, the pump signal 3, 3a, having a first power P1, induces a first pump current 10 in the at least one parametric resonator circuit 5, wherein the at least one parametric resonator circuit 5 is operated below its oscillation threshold and generates a first output signal 11 by amplifying a first input signal 13, which is provided due to a magnetic-resonance (MR) measurement, wherein an external receiving device 17 receives the first output signal 11, wherein, in a second detection mode, the pump signal 3, 3b, having a second power P2, induces a second pump current 12 in the at least one parametric resonator circuit 5, wherein the at least one parametric resonator circuit 5 is operated above its oscillation threshold and generates a second output signal 14, wherein the second output signal 14 is modulated with a second input signal 15, wherein the second input signal 15 is provided by at least one neuronal probe device 16, connected to the at least one parametric resonator circuit 5, wherein the external receiving device 17 receives the second output signal 4.

The system comprises an MRI scanner device 23 that enables the visualization of organs, organ function, and/or other tissue within a body, in particular a brain of a subject 24. The subject may be an animal, such as a rat, a monkey or a human. The MRI scanner device 23 comprises a primary magnet 25 that generates a uniform magnetic field B0 that is applied across the body of the subject 24 under observation. The magnetic field B0 is preferably in the range of between approx. 3 T to approx. 21 T, more preferably in the range of between approx. 7 T to approx. 14 T. The subject is arranged in a bore. In case of animal studies, the bore has a bore diameter of preferably in the range of between 50 cm to 6 cm, more preferably 12 cm.

The MRI scanner device 23 further comprises at least one smaller gradient magnet 26 which generates a gradient magnetic field BG. The magnetic field B0 aligns the nuclear spins, in particular of the hydrogen atoms, in the tissue. The nuclear magnetic spins precess with the so-called Larmour frequency about the magnetic field direction like gyroscopes. Due to the additional gradient magnetic field BG, the Larmour frequency is altered along the gradient magnetic field BG. Thus, the gradient magnet allows image "slices" of the body to be created.

The MRI scanner device 23 further comprises an RF-signal generator 27, which applies a radio frequency (RF)-pulse BRF, perpendicular to said magnetic field B0 of the primary magnet. This RF-pulse causes the nuclear spins to tilt away from the alignment direction. In the absence of the RF-pulse BRF, the nuclear spins relax to the lower energy state and align with the magnetic field B0. The surplus energy gained by the RF-pulse is emitted by a RF-signal. This signal is the first input signal of the wireless detection unit 4.

The system 1 comprises a device for image processing 20. The external receiving device 17 transmits the first 11 and the second output signal 14 to the device for image processing 20. The external receiving device 17 comprises a receiving coil, which detects the first 11 and the second output signal 14 inductively. The system 1 may further comprise a user interface 28 which comprises an input device, such as a keyboard, and/or an output device, such as a display.

The pump signal generator (2) may also be able to emit more than one pump signals (3, 3a, 3b) with a first power P1 and a second power P2 simultaneously.

Embodiments of the wireless detection unit 4 are shown in the FIGS. 2 to 5. The wireless detection unit 4 for use in a magnetic-resonance (MR) measurement comprises at least one parametric resonator circuit 5 with multiple resonance modes, wherein the at least one parametric resonator circuit 5 comprises at least two varactors 6,7, at least one capacitor 8 and at least one inductance 9, wherein, in a first detection mode, a pump signal 3, 3a, having a first power P1, induces a first pump current 10 in the at least one parametric resonator circuit 5, wherein the at least one parametric resonator circuit 5 is operated below its oscillation threshold and generates a first output signal 11 by amplifying a first input signal 13, which is provided due to a magnetic-resonance (MR) measurement, wherein, in a second detection mode, the pump signal 3, 3b, having a second power P2, induces a second pump current 12 in the at least one parametric resonator circuit 5, wherein the at least one parametric resonator circuit 5 is operated above its oscillation threshold and generates a second output signal 14, wherein the second output signal 14 is modulated with a second input signal 15, wherein the second input 15 signal is provided by a neuronal probe device 16, connected to the at least one parametric resonator circuit 5.

Figure 2:
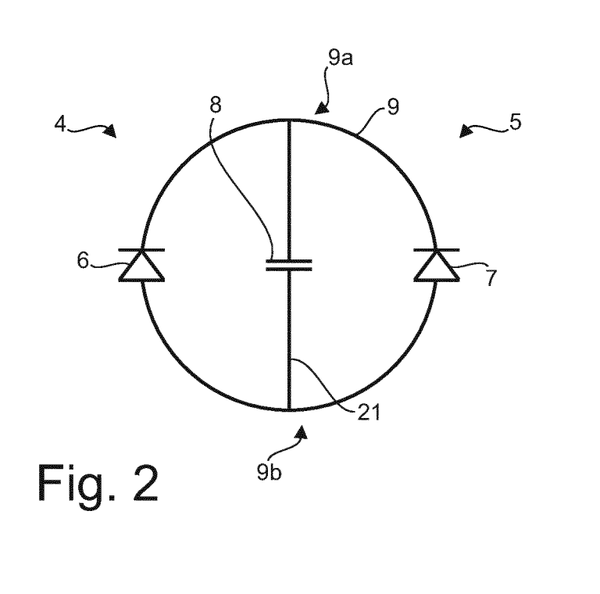
FIG. 2 shows a wireless detection unit according to one embodiment.
Figure 3:
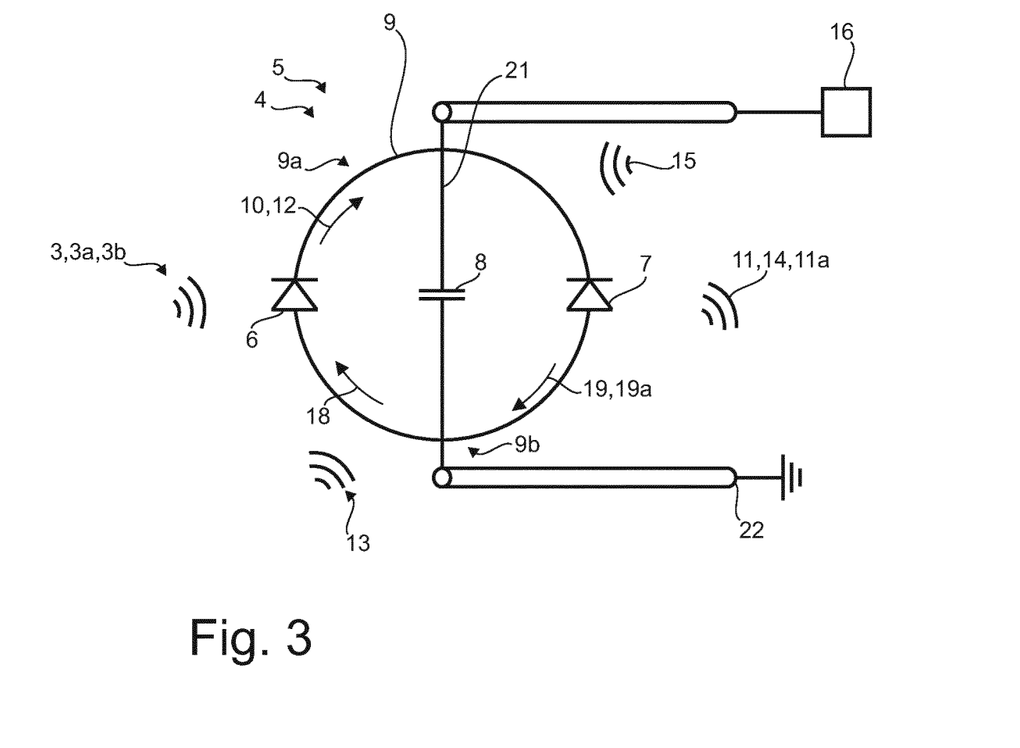
FIG. 3 shows a wireless detection unit according to one embodiment.

The at least one parametric resonator circuit 5 is a parallel circuit comprising two varactors 6, 7 and one capacitor 8 in the center leg 21 of the parallel circuit. The cathode of the first varactor 6 is connected with the first terminal of the capacitor 8 and the cathode of the second varactor 7 by a first connection. The anode of the first varactor 6 is connected with the second terminal of the capacitor 8 and the anode of the second varactor 7 by a second connection. The first and the second connection form a first 9a and a second inductance 9b. Thus, the parametric resonator circuit 5 is a LC-circuit with multiple resonance modes. The at least one parametric resonator circuit is a wire loop by which the two varactors 6, 7 are connected, and with a center leg 21 in which the capacitor 8 is arranged. The wire loop has a diameter in the range of between 5 mm to 15 mm, preferably 9 mm. For a 9 mm loop, a capacitor 8 with a capacity of 7.5 pF may be chosen. The capacitor 8 may be in the form of a chip capacitor.

The wireless detector 4 in FIG. 2 may be used for MRI measurements. The use of such a device has the advantage that no additional power source in the form of a battery is required. Further, the transmission of the measured signal does not require the use of a cable.

The device shown in FIG. 3 has the additional advantage that next to the input signals 11, stemming from the MRI-measurement, signals 15 stemming from at least one neuronal probe device 16 may be transmitted wirelessly by the same detection unit 4. The detection mode is switchable, just by applying different powers P1 and P2 of the pump signal 3, 3a, 3b. A first pump signal 3, 3a, having the first power P1, would be applied for the first detection mode, in which the first input signal 11 is detected and transmitted to the external receiving device 17. A second pump signal 3, 3b, having the second power P2, would be applied for the second detection mode, in which the second input signal 15 is detected and transmitted to the external receiving device 17.

The at least one neuronal probe device 16 is connected to the first terminal of the capacitor 8 in the center leg 21 of the parallel circuit, wherein the second terminal of the capacitor 8 in the center leg of the parallel circuit is connected to a ground electrode 22. Alternatively, the neuronal probe device 16 could be connected to the first and the second terminal of the capacitor 8.

The neuronal probe device may preferably comprise at least one EEG-probe, which detects the differences of electrical potentials due to brain activity.

In the first detection mode, the power P1 of the first pump signal 3, 3a does not provide enough gain to compensate for the resonator loss. Thus, the parametric resonator circuit is operated in the amplifier mode. Parametric oscillation occurs when the parametric amplification compensates the loss of a resonator at the resonance frequency. Thus, the parametric resonator circuit is operated in the oscillator mode. This is the case in the second detection mode, when the power P2 of the second pump signal 3, 3b does provide enough gain to compensate for the resonator loss.

The first 3, 3a and the second pump signal 3, 3b have a third frequency $\omega 3$, wherein the parametric resonator circuit 5 resonates at the third frequency $\omega 3$ and generates the first pump current 10 or the second pump current 12, depending on the first power P1 and a second power P2. In the first resonance mode, the parametric resonator circuit 5 is tuned to match the pump signal. Thus, when the parametric resonator circuit 5 is operated below the oscillation threshold, the pump signal 3a, which serves as power source, has a power P1 and the third frequency $\omega 3$.

The first input signal 11 has a first frequency $\omega 1$, wherein the parametric resonator circuit 5 resonates at the first frequency $\omega 1$ and generates a first input current 18. Thus, in the second resonance mode, the parametric resonator circuit 5 is tuned to match a first input signal, which is provided due to a magnetic-resonance (MR) measurement. The varactor 6, 7 generates a resulting current 19, based on the first input current 18 and the first pump current 10. The varactor 6,7 has a high Q zero biased condition and performs frequency mixing. Thus, the resulting current 19 is generated by mixing the first input current 18 and the first pump current 10. The parametric resonator circuit 5 resonates at a second frequency $\omega 2$, in response to the resulting current 19, to generate the first output signal 11. The first output signal, also called "idler signal", preferably has the frequency $\omega 2=\omega 3-\omega 1$ or $\omega 2=\omega 3+\omega 1$. It is preferred that the first output signal/the corresponding resulting current 19 mixes again with the pump signal at $\omega 3$/the corresponding pump current 10. In doing so, a secondary resulting current 19a and a corresponding secondary first output signal 11a with a frequency $\omega 4$ are generated. The frequency $\omega 4$ is essentially equal to the first frequency $\omega 1$: $\omega 4=|\omega 3-\omega 2|=|\omega 3-(\omega 3\pm\omega 1)|=|\omega 1|$. Thus, an amplified signal 11a with the frequency $\omega 1$ may be generated and emitted by the parametric resonator circuit 5.

Preferably, the second frequency $\omega 2$ is nearly equal to the first frequency $\omega 1$, wherein the second frequency $\omega 2$ differs from the first frequency $\omega 1$ by a difference frequency $\omega d$, which is in the range between 5 kHz to 100 kHz, preferably between 20 kHz to 80 kHz, more preferably between 40 kHz to 80 kHz. Preferably, the difference frequency $\omega d$ is larger than the receiver bandwidth of the MRI-system. The MRI-signal is typically frequency-encoded by a spatially varying gradient field. This gradient slightly alters the precession frequencies of the nuclear spins. The bandwidth of the gradient field is typically in the range between 5 kHz to 100 kHz, preferably 50 kHz. Advantageously, the difference frequency $\omega d$ is about 5 kHz to 20 kHz larger than the imaging bandwidth. Preferably, the difference frequency $\omega d$ is about 10 kHz larger than the imaging bandwidth. Thus, given a typical bandwidth of 50 kHz, the difference frequency $\omega d$ would preferably be 60 kHz. The advantage of such a design is that the frequencies $\omega 1$ and $\omega 2$ may conveniently be differentiated.

Advantageously, the third frequency $\omega 3$ is essentially twice the first frequency $\omega 1$. By making the idler frequency $\omega 2$ close enough to the Larmour frequency $\omega 1$, and making $\omega 3$ approximately twice $\omega 1$, it is possible for $\omega 1$ and $\omega 2$ to share a single circuit mode. Preferably, the parametric resonator circuit 5 is then a double frequency resonator. The pumping frequency is preferably in the range between 1 GHz to 1.2 GHz. The frequencies $\omega 1$, $\omega 2$ would therefore be in the range between 500 MHz to 600 MHz.

Figure 4A:
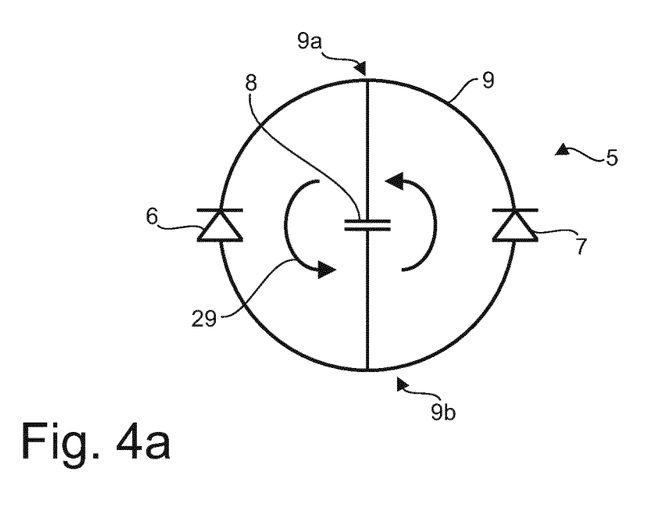
FIG. 4a, b show a wireless detection unit according to one embodiment.
Figure 4B:
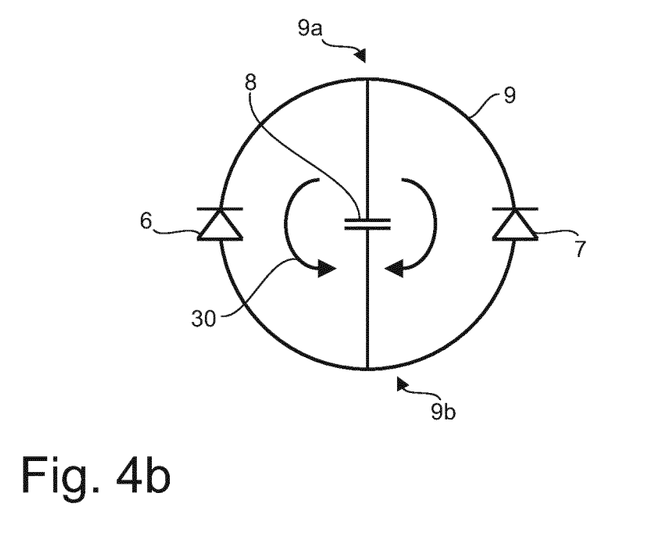

In another embodiment shown in FIGS. 4a, 4b, the parametric resonator circuit 5 can support anti-symmetric current flow 29 and symmetric current flow 30. The anti-symmetric mode 29, which corresponds to FIG. 4a, can be tuned to the Larmour frequency $\omega 1$ by the two varactor diodes on the left and right arches; it can create a dipole field pattern that is sensitive to the first input signal 13, in the form of a MRI signal. The symmetric mode 30, which corresponds to FIG. 4b, can be tuned by a tunable capacitor 8 in the center leg; it can create a butterfly field pattern that is sensitive to the external pump signal at $\omega 3$. The parametric resonator circuit 5 may also be connected to a neuronal probe device 16.

In the second detection mode, the parametric resonator (oscillator) circuit 5 oscillates at the frequency $\omega c$, which is half the frequency of the pump signal $\omega 3$. For example, $\omega c$ is 600 MHz. Naturally, the output signal 14 would then have a carrier frequency $\omega c$ of 600 MHz. Due to the second input signal 15 provided by the neuronal probe, the sidebands of the oscillation peak of the second output signal are modulated. The amplitude of sidebands will change linearly with the strength of the neuronal signal.

Preferably, such a modulation is a modulation of the amplitude of the second output signal and/or the frequency of the second output signal. Advantageously, the second input signal is encoded as sidebands of the oscillation peak of the second output signal. The frequency of the signal from the neuronal probe device 16 is within +/−1 kHz from the carrier frequency $\omega c$.

Although, during MRI detection, the MR signal intensity is slightly modulated by EEG signal, this modulation will not affect the results of most MR experiments. Furthermore, this intensity modulation may be removed from the output signal 11 by comparing multi-band signals generated by the parametric resonator circuit. During EEG detection, the contribution of MRI signals on the oscillation signal is negligible.

The at least one parametric resonator may be embedded in a planar thin film element. Preferably, the thin film element consists of a polyimide, more preferably of a copper-clad polyimide. The at least one parametric amplifier circuit in the form of a wire loop, by which the two varactors are connected, and with a center leg in which the capacitor is arranged, is laminated by the polyimide or another suitable material. Advantageously, such a thin film element has a diameter in the range between 2 to 20 mm, preferably between 5 to 15 mm, more preferably between 8 to 12 mm. Advantageously, such a thin film element has a thickness in the range between 1 to 6 mm, preferably between 2 to 4 mm.

The wireless detection unit 4 may comprise at least two parametric resonator circuits 5, 5a, 5b. The at least two parametric resonator circuits 5, 5a, 5b overlap spatially and no electrical connection exists between the at least two parametric resonator circuits 5, 5a, 5b. Hereby, each parametric resonator circuit 5, 5a, 5b is tuned to resonate at a different third frequency ω3a, ω3b, such that, by applying a pump signal 3, 3a, 3b with the third frequency ω3a, ω3b, one parametric resonator circuit 5, 5a, 5b can be activated.

Figure 5A:
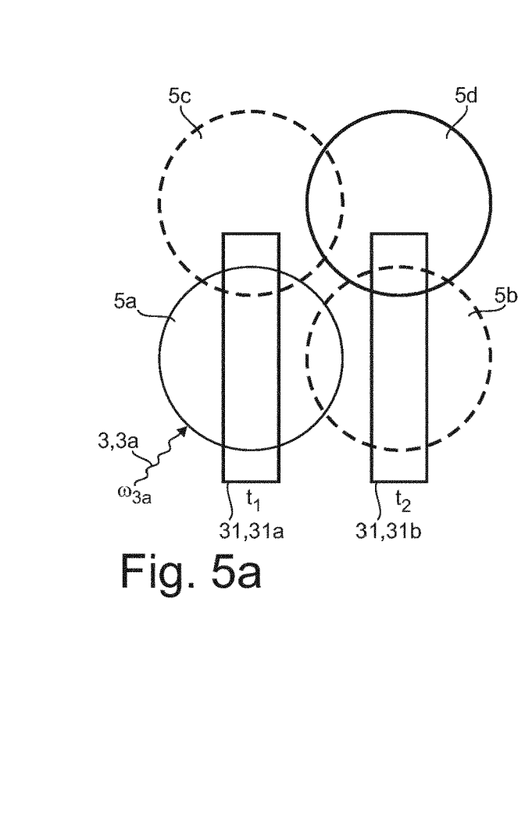
FIG. 5a, b, c show a wireless detection unit according to one embodiment.
Figure 5B:
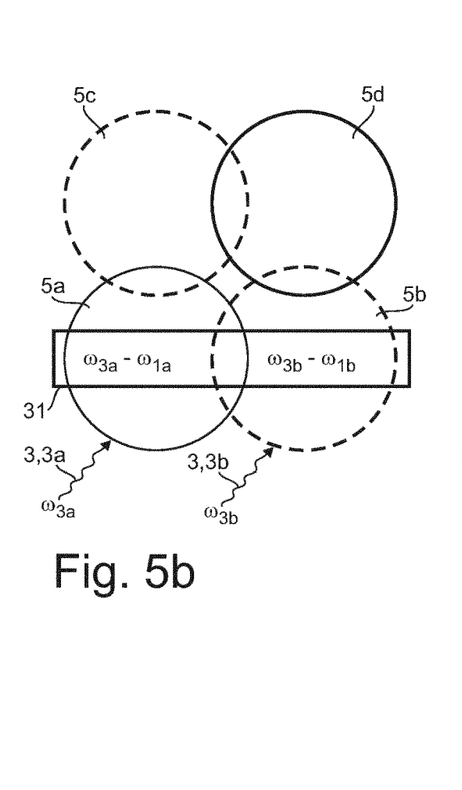
Figure 5C:
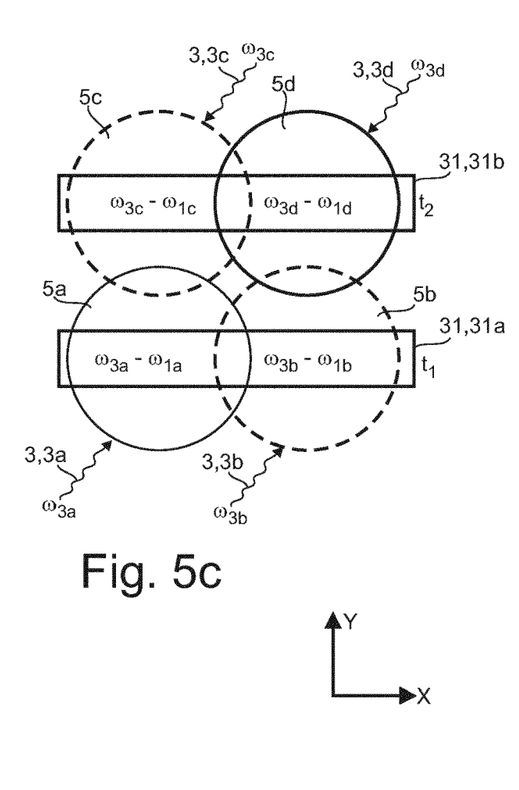

In FIGS. 5a, 5b and 5c, an embodiment is shown, in which the wireless detection unit comprises four parametric resonator circuits 5, 5a, 5b, 5c, 5d, which are arranged in a quadrilateral. For simplicity reasons, the actual components, like the two varactors and the capacitor in the center leg, are not shown in the FIGS. 5a, 5b and 5d. Each resonator circuit 5, 5a, 5b, 5c, 5d overlaps spatially with two adjacent resonator circuits 5, 5a, 5b, 5c, 5d. Each parametric resonator circuit 5, 5a, 5b, 5c, 5d is tuned to resonate at a different third frequency ω3a, ω3b, ω3c, ω3d, such that, by applying a pump signal 3, 3a, 3b with a third frequency ω3a, ω3b, ω3c, ω3d, one parametric resonator circuit 5, 5a, 5b, 5c, 5d can be activated. It is conceivable that only one of the parametric resonator circuits 5, 5a, 5b, 5c, 5d is connected with a neuronal probe device according to FIG. 3. The other three parametric resonator circuits 5, 5a, 5b, 5c, 5d would then have no such connection and would be embodiments according to FIG. 2. It is conceivable that more than one parametric resonator circuit 5, 5a, 5b, 5c, 5d is connected with a neuronal probe device 16. Finally, it is also conceivable that all of the parametric resonator circuits 5, 5a, 5b, 5c, 5d are connected with a neuronal probe device 16.

An arrangement according to FIGS. 5 to 5c has the advantage of enlarging the field of view beyond an individual parametric resonator circuit 5, 5a, 5b, 5c, 5d and without sacrificing detection sensitivity. The overlap between the parametric resonator circuits 5, 5a, 5b, 5c, 5d is small and serves the purpose of minimizing signal voids. By making each individual parametric resonator circuit 5, 5a, 5b, 5c, 5d sensitive to a unique pumping frequency ω3a, ω3b, ω3c, ω3d, each parametric resonator circuit 5, 5a, 5b, 5c, 5d can individually be turned on or off by the wireless pump signal.

In FIG. 5a, a sequential acquisition mode of the wireless detection unit 4 is displayed. At a time t1, only the left-bottom parametric resonator circuit 5a is tuned to respond to a pump signal 3, 3a with a frequency at ω3a, so that only signals by this resonator bottom parametric resonator circuit 5a are detected. As already outlined, the use of the at least one gradient magnet 26 allows to divide the region to detect in acquisition slices 31. In FIG. 5a, the left-bottom parametric resonator circuit 5a is in direct contact with the first acquisition slice 31a. Thus, at the time t1, the first input signal 13 from the first acquisition slice 31a is detected. At the time t2, the parametric resonator circuit 5b is activated with a pump signal 3, 3b at a frequency ω3b and the first input signal 13 from the second acquisition slice 31b is detected.

In FIG. 5b, a simultaneous acquisition mode of the wireless detection unit 4 is displayed. The parametric resonators 5a and 5b are activated simultaneously by applying two pump signals 3, 3a, 3b with the frequencies ω3a and ω3b simultaneously. The first input signal 13 from the acquisition slice 31 is detected by both parametric resonators 5a and 5b. The first output signal 11 from each parametric resonator 5a and 5b is individually encoded, such that it may be assigned to each parametric resonator 5a and 5b. Such an encoding may already be apparent by the choice of the third frequency ω3a and ω3b, since the idler frequency is ω3a−ω1a and ω3b−ω1b. By mathematically separating the signal contributions of each parametric resonator 5a and 5b at their respective frequency bands, the single-channel receiver may be multiplexed into multiple channels, but without the need for the expensive console.

In FIG. 5c, a hybrid acquisition mode of the wireless detection unit 4, which is a combination of a sequential acquisition mode and a simultaneous acquisition mode of the wireless detection unit 4, is shown. Along the horizontal direction X of the quadrilateral, the first acquisition slice 31, 31a extends. At the time t1, the parametric resonators 5a and 5b are activated simultaneously by applying two pump signals 3, 3a, 3b with the frequencies ω3a and ω3b simultaneously. At the time t2, the parametric resonators 5c and 5d are activated simultaneously by applying two pump signals 3, 3c, 3d with the frequencies ω3c and ω3d simultaneously. These acquisition paradigms allow to run specific imaging sequences based on the acquisition modes.

All the features disclosed in the application documents are claimed as being essential to the invention if, individually or in combination, they are novel over the prior art.

LIST OF REFERENCE NUMERALS 1 system
2 pump signal generator
3 pump signal
3a pump signal with frequency ω3a
3b pump signal with frequency ω3b
3c pump signal with frequency ω3c
3d pump signal with frequency ω3d
4 wireless detection unit
5 parametric resonator circuit
5a first parametric resonator circuit
5b second parametric resonator circuit
5c third parametric resonator circuit
5d fourth parametric resonator circuit
6 varactor
7 varactor
8 capacitor
9 inductance
9a first inductance
9b second inductance
10 first pump current
11 first output signal
11a secondary first output signal
12 second pump current
13 first input signal
14 second output signal
15 second input signal
16 neuronal probe device
17 external receiving device
18 first input current
19 resulting current
19a secondary resulting current
20 device for image processing 21 center leg
22 ground electrode
23 MRI scanner device
24 subject
25 primary magnet
26 gradient magnet
27 RF-signal generator
28 user interface
29 symmetric current flow
30 anti-symmetric current flow
31 acquisition slices
31a first acquisition slice
31b second acquisition slice
B0 magnetic field of primary magnet
BG gradient magnetic field
BRF RF-pulse
t1 first time
t2 second time
X horizontal direction
Y vertical direction

The invention claimed is:

1. A 8system for imaging, comprising a pump signal generator configured to emits at least one pump signal, in the radio frequency (RF) range with a first power and a second powers P-2, a wireless detection unit, comprises at least one parametric resonator circuit with multiple resonance modes, wherein the at least one parametric resonator circuit (5 comprises at least two varactors, at least one capacitor and at least one inductance, an external receiving device configured to receive a first output signal or a second output signal; wherein, in a first detection mode, the pump signal, is at the first power, and induces a first pump current in the at least one parametric resonator circuit; the at least one parametric resonator circuit is operated below its oscillation threshold and generates a-the first output signal by amplifying a first input signal, which is provided due to a magnetic-resonance (MR) measurement, wherein, in a second detection mode the pump signal, is at a-the second power, and induces a second pump current in the at least one parametric resonator circuitry, the at least one parametric resonator circuit is operated above its oscillation threshold and generates a-the second output signal; and, wherein the second output signal is modulated with a second input signal, that is provided by at least one neuronal probe device, connected to the at least one parametric resonator circuit.

2. The system according to claim 1, wherein the first input signal has a first frequency co, the parametric resonator circuit (5 resonates at the first frequency o1 and generates a first input current, wherein the pump signal, has a third frequency c3, wherein the parametric resonator circuit resonates at the third frequency c3 and generates the first pump current or the second pump current, depending on the first power and a-the second power P-2, wherein one of the at least two varactors generates a resulting current, based on the first input current and the first pump current, wherein the parametric resonator circuit resonates at a second frequency o2, in response to the resulting current to generate the first output signal.

3. The system according to claim 2, wherein the second frequency o2 is nearly equal to the first frequency co, wherein the second frequency w2 differs from the first frequency w1 by a difference frequency od, which is between 10 kHz to 100 kHz.

4. The system according to claim 1 further comprises a device for image processing, wherein the external receiving device transmits at least one of the first or the second output signal to the device for image processing.

5. The system according to claim 1, wherein the at least one parametric resonator circuit is a parallel circuit comprising two varactors, and one capacitor in a center leg of the parallel circuit, wherein the cathode of the first varactor is connected with the first terminal of the capacitor and the cathode of the second varactor by a first connection, wherein the anode of the first varactor is connected with the second terminal of the capacitor and the anode of second varactor by a second connection, wherein the first and the second connection form a first and a second inductance, wherein the at least one parametric resonator circuit is a wire loop by which the two varactors, are connected and with a-the center leg in which the capacitor is arranged.

6. The system according to claim 5, wherein the at least one neuronal probe device is connected to the first terminal of the at least one capacitor (8) in the center leg f the parallel circuit, wherein the second terminal of the at least one capacitor in the center leg of the parallel circuit is connected to a ground electrode.

7. The system according to claim 1 wherein the at least one parametric resonator circuit is integrated in a planar thin film element, and wherein the planar thin film element includes a polyimide.

8. The system according to claim 1 wherein the wireless detection unit comprises at least two parametric resonator circuits, that overlap spatially, wherein no electrical connection exists between the at least two parametric resonator circuits, and each parametric resonator circuit, is tuned to resonate at a different third frequency o3a, o3b, such that, by applying a pump signal, with the third frequency o3a, o3b, one parametric resonator circuit, can be activated.

9. The system according to claim 1, wherein the wireless detection unit comprises four parametric resonator circuits, which are arranged in a quadrilateral, wherein each resonator circuit, overlaps spatially with at least one adjacent resonator circuit, and is tuned to resonate at a different third frequency o3a, o3b, o3c, o3d, such that, by applying a pump signal, with a third frequency o3a, o3b, o3c, o3d, one parametric resonator circuit, an be activated.

10. The system according to one of the claim 8 or 9, wherein the parametric resonator circuits, are sequentially or simultaneously activatable, wherein, for a simultaneous activation of at least two parametric resonator circuits, at least two different pump signals, with a third frequency o3a, o3b, o3c, o3d, are used at the same time.

11. A wireless detection unit for use in a magnetic-resonance (MR) measurement comprising at least one parametric resonator circuit with multiple resonance modes, wherein the at least one parametric resonator circuit comprises at least two varactors, at least one capacitor and at least one inductance, wherein, in a first detection mode, a pump signal, having a first power, induces a first pump current in the at least one parametric resonator circuit, the at least one parametric resonator circuit is operated below its oscillation threshold and generates a first output signal by amplifying a first input signal, which is provided due to a magnetic-resonance (MR) measurement, wherein an external receiving device receives the first output signal, wherein, in a second detection mode the pump signal, having a second power, induces a second pump current in the at least one parametric resonator circuit, the at least one parametric resonator circuit is operated above its oscillation threshold and generates a second output signal, the second output signal is modulated with a second input signals, the second input signal is provided by at least one neuronal probe device, connected to the at least one parametric resonator circuit.

12. The wireless detection unit according to claim 11, wherein the first input signal has a first frequency ol, the at least one parametric resonator circuit resonates at the first frequency co and generates a first input current, and the pump signal, has a third frequency o3; wherein the at least one parametric resonator circuit (5) resonates at the third frequency w3 and generates the first pump current or the second pump current, depending on the first power and a second power; wherein at least one varactor (6) generates a resulting current, based on the first input current and the first pump current, wherein the at least one parametric resonator circuit resonates at a second frequency C2, in response to the resulting current to generate the first output signal, wherein the second frequency o2 is nearly equal to the first frequency ol; wherein the second frequency o2 differs from the first frequency ol by a difference frequency od, which is in the range between 10 kHz to 100 kHz, and wherein the third frequency c3 is essentially twice the first frequency Oi.

13. The wireless detection unit according to claim 11, wherein the at least one parametric resonator circuit is a parallel circuit comprising the at least two varactors, and the at least one capacitor in a center leg of the parallel circuit; wherein the cathode of a first varactor is connected with the first terminal of the at least one capacitor and the cathode of the second varactor by a first connection; wherein the anode of a first varactor is connected with the second terminal of the at least one capacitor and the anode of the second varactor by a second connection; wherein the first and the second connection form a first and a second inductance, wherein the at least one parametric resonator circuit is a wire loop by which the two varactors, are connected, and with a-the center leg in which the capacitor is arranged; wherein the at least one neuronal probe device is connected to the first terminal of the capacitor in the center leg of the parallel circuit; and wherein the second terminal of the capacitor in the center leg of the parallel circuit is connected to a ground electrode.

14. The wireless detection unit according to claim 11, wherein the wireless detection unit comprises at least two parametric resonator circuits, wherein the at least two parametric resonator circuits, overlap spatially, wherein no electrical connection exists between the at least two parametric resonator circuits, wherein each parametric resonator circuit, is tuned to resonate at a different third frequency o3a, o3b, such that, by applying a pump signal, with a third frequency o3a o3b, one parametric resonator circuit, can be activated.

15. The wireless detection unit according to claim 11, wherein the parametric resonator circuits, are sequentially or simultaneously activatable, and wherein, for a simultaneous activation of at least two parametric resonator circuits, at least two different pump signal, with a third frequency o3a, o3b, o3c, o3d, are used at the same time.

* * * * *

UNITED STATES PATENT AND TRADEMARK OFFICE
CERTIFICATE OF CORRECTION

| | |
|---|---|
| PATENT NO. | : 11,637,527 B2 |
| APPLICATION NO. | : 17/618064 |
| DATED | : April 25, 2023 |
| INVENTOR(S) | : Xin Yu et al. |

It is certified that error appears in the above-identified patent and that said Letters Patent is hereby corrected as shown below:

In the Claims

Column 15, Claim 1, Line 22, "8system" should be --system--.

Column 15, Claim 1, Line 25, "powers P-2," should be --power;--.

Column 15, Claim 1, Line 27, "circuit (5" should be --circuit--.

Column 15, Claim 1, Line 28, "varactors," should be --varactors--.

Column 15, Claim 1, Line 29, "inductance," should be --inductance;--.

Column 15, Claim 1, Line 31, "mode, the pump signal," should be --mode; the pump signal--.

Column 15, Claim 1, Line 32, "power," should be --power--.

Column 15, Claim 1, Line 35, "a-the" should be --the--.

Column 15, Claim 1, Line 37, "measurement," should be --measurement;--.

Column 15, Claim 1, Line 38, "mode the pump signal, is at a-the" should be --mode; the pump signal is at the--.

Column 15, Claim 1, Line 40, "circuitry," should be --circuit;--.

Column 15, Claim 1, Line 42, "a-the" should be --the--.

Column 15, Claim 1, Line 42, "and," should be --and--.

Column 15, Claim 1, Line 44, "signal," should be --signal--.

Signed and Sealed this
Third Day of October, 2023

*Katherine Kelly Vidal*

Katherine Kelly Vidal
*Director of the United States Patent and Trademark Office*

Column 15, Claim 1, Line 44, "device," should be --device--.

Column 15, Claim 2, Line 47, "co" should be --$\omega 1$--.

Column 15, Claim 2, Line 48, "circuit (5" should be --circuit--.

Column 15, Claim 2, Line 48, "ol" should be --$\omega 1$--.

Column 15, Claim 2, Line 49, "signal," should be --signal--.

Column 15, Claim 2, Line 50, "c3" should be --$\omega 3$--.

Column 15, Claim 2, Line 51, "c3" should be --$\omega 3$--.

Column 15, Claim 2, Line 53, "a-the" should be --the--.

Column 15, Claim 2, Line 53, "power P-2" should be --power--.

Column 15, Claim 2, Line 58, "o2" should be --$\omega 2$--.

Column 15, Claim 3, Line 60, "o2" should be --$\omega 2$--.

Column 15, Claim 3, Line 60, "co" should be --$\omega 1$--.

Column 15, Claim 3, Line 61, "w2" should be "$\omega 2$".

Column 15, Claim 3, Line 62, "w1" should be --$\omega 1$--.

Column 15, Claim 3, Line 62, "od" should be --$\omega d$--.

Column 15, Claim 4, Line 64, "1" should be --1,--.

Column 16, Claim 5, Line 8, "of second" should be --of the--.

Column 16, Claim 5, Line 12, "varactors," should be --varactors--.

Column 16, Claim 5, Line 12, "a-the" should be --the--.

Column 16, Claim 6, Line 16, "capacitor (8) in" should be --capacitor in--.

Column 16, Claim 6, Line 16, "leg f the" should be --leg of the--.

Column 16, Claim 7, Line 20, "1" should be --1,--.

Column 16, Claim 8, Line 24, "1" should be --1,--.

Column 16, Claim 8, Line 26, "circuits," should be --circuits--.

Column 16, Claim 8, Line 28, "circuits," should be --circuits--.

Column 16, Claim 8, Line 29, "o3a, o3b" should be --$\omega$3a, $\omega$3b--.

Column 16, Claim 8, Line 30, "o3a, o3b" should be --$\omega$3a, $\omega$3b--.

Column 16, Claim 9, Line 37, "o3a, o3b, o3c, o3d" should be --$\omega$3a, $\omega$3b, $\omega$3c, $\omega$3d--.

Column 16, Claim 9, Line 38, "o3a, o3b, o3c, o3d" should be --$\omega$3a, $\omega$3b, $\omega$3c, $\omega$3d--.

Column 16, Claim 9, Line 39, "circuit, an" should be --circuit can--.

Column 16, Claim 10, Line 40, "claim 8 or 9" should be --claims 8 or 9--.

Column 16, Claim 10, Line 44, "o3a, o3b," should be --$\omega$3a, $\omega$3b,--.

Column 16, Claim 10, Line 45, "o3c, o3d," should be --$\omega$3c, $\omega$3d,--.

Column 16, Claim 11, Line 47, "comprising" should be --comprising:--.

Column 16, Claim 11, Lines 49-50, "comprises" should be --comprises:--.

Column 16, Claim 11, Line 50, "varactors," should be --varactors--.

Column 16, Claim 11, Line 50, "capacitor" should be --capacitor;--.

Column 16, Claim 11, Line 51, "mode," should be --mode:--.

Column 16, Claim 11, Line 53, "circuit," should be --circuit;--.

Column 16, Claim 11, Line 58, "signal," should be --signal;--.

Column 16, Claim 11, Line 59, "mode" should be --mode;--.

Column 16, Claim 11, Line 63, "signal," should be --signal;--.

Column 16, Claim 11, Line 64, "signals," should be --signal;--.

Column 17, Claim 12, Line 2, "ol" should be --$\omega$1--.

Column 17, Claim 12, Line 4, "co" should be --$\omega$1--.

Column 17, Claim 12, Line 5, "signal," should be --signal--.

CERTIFICATE OF CORRECTION (continued)
U.S. Pat. No. 11,637,527 B2

Column 17, Claim 12, Line 5, "o3" should be --ω3--.

Column 17, Claim 12, Line 6, "circuit (5) resonates" should be --circuit resonates--.

Column 17, Claim 12, Line 7, "w3" should be --ω3--.

Column 17, Claim 12, Line 9, "varactor (6) generates" should be --varactor generates--.

Column 17, Claim 12, Line 11, "current," should be --current;--.

Column 17, Claim 12, Line 12, "C2" should be --ω2--.

Column 17, Claim 12, Line 13, "signal," should be --signal;--.

Column 17, Claim 12, Line 14, "o2" should be --ω2--.

Column 17, Claim 12, Line 15, "ol;" should be --ω1--.

Column 17, Claim 12, Line 15, "o2" should be --ω2--.

Column 17, Claim 12, Line 16, "ol" should be --ω1--.

Column 17, Claim 12, Line 16, "od" should be --ωd--.

Column 17, Claim 12, Line 17, "kHz,," should be --kHz;--.

Column 17, Claim 12, Line 18, "c3" should be --ω3--.

Column 17, Claim 12, Line 18, "Oi" should be --ω1--.

Column 17, Claim 13, Line 21, "varactors," should be --varactors--.

Column 18, Claim 13, Line 5, "a-the" should be --the--.

Column 18, Claim 14, Line 18, "o3a, o3b" should be "ω3a, ω3b--.

Column 18, Claim 14, Line 20, "o3a, o3b" should be --ω3a, ω3b--.

Column 18, Claim 15, Lines 26-26, "o3a, o3b, o3c, o3d" should be --ω3a, ω3b, ω3c, ω3d--.